United States Patent [19]

Mollenauer

[11] Patent Number: 5,643,301
[45] Date of Patent: Jul. 1, 1997

[54] CANNULA ASSEMBLY WITH SQUEEZE OPERATED VALVE

[75] Inventor: Kenneth H. Mollenauer, Santa Clara, Calif.

[73] Assignee: General Surgical Innovations, Inc., Palo Alto, Calif.

[21] Appl. No.: 475,114

[22] Filed: Jun. 7, 1995

[51] Int. Cl.⁶ .................................... A61B 17/32
[52] U.S. Cl. .................. 606/167; 604/167; 604/169
[58] Field of Search ........................... 606/167, 170, 606/185; 604/167, 169, 185, 164, 264

[56] References Cited

U.S. PATENT DOCUMENTS 5,057,084  10/1991  Ensminger et al. ............... 604/167
5,071,411  12/1991  Hillstead ............................ 604/246
5,514,098  5/1996  Pfoslgraf et al. .................. 604/167

*Primary Examiner*—Michael Buiz
*Assistant Examiner*—Kevin Truong
*Attorney, Agent, or Firm*—Lyon & Lyon LLP

[57] ABSTRACT

An improved valve for cannulas and endoscopic access ports used during insufflation. A duckbill valve is provided which can accommodate the passage of endoscopic instruments such as endoscope, graspers and scissors and form a seal around the shaft of these instruments, thereby maintaining insufflation pressure. The access port housing around the duckbill valve is squeezable, so that the duckbill valve may be squeezed open by squeezing the access port housing, thereby facilitating removal of endoscopic instruments without the need to manipulate a valve fitting.

14 Claims, 3 Drawing Sheets

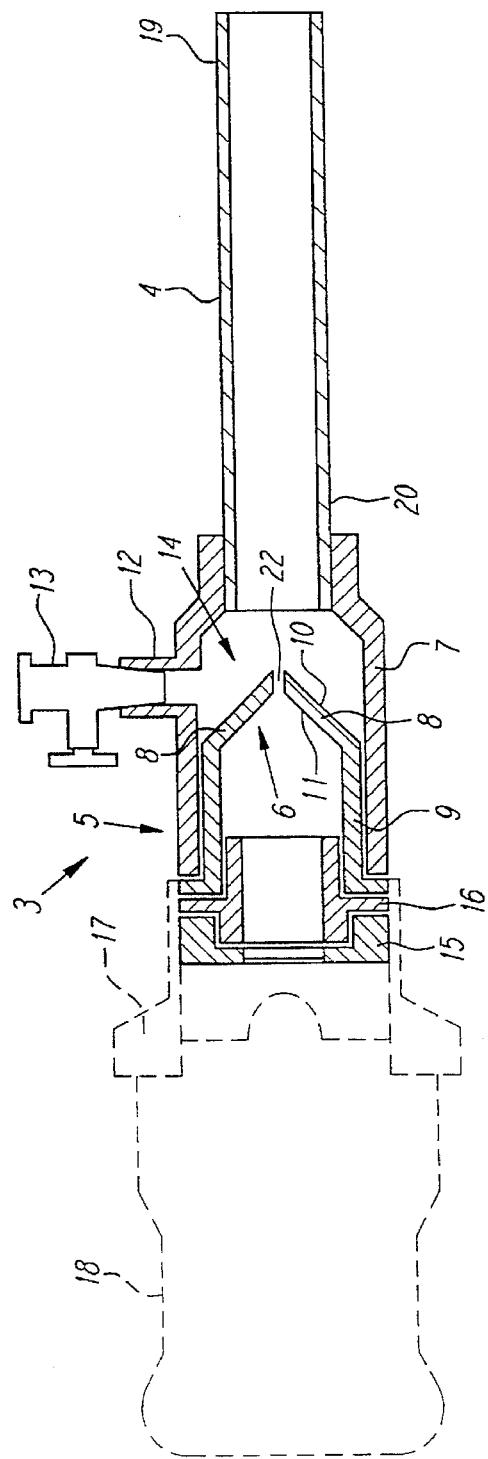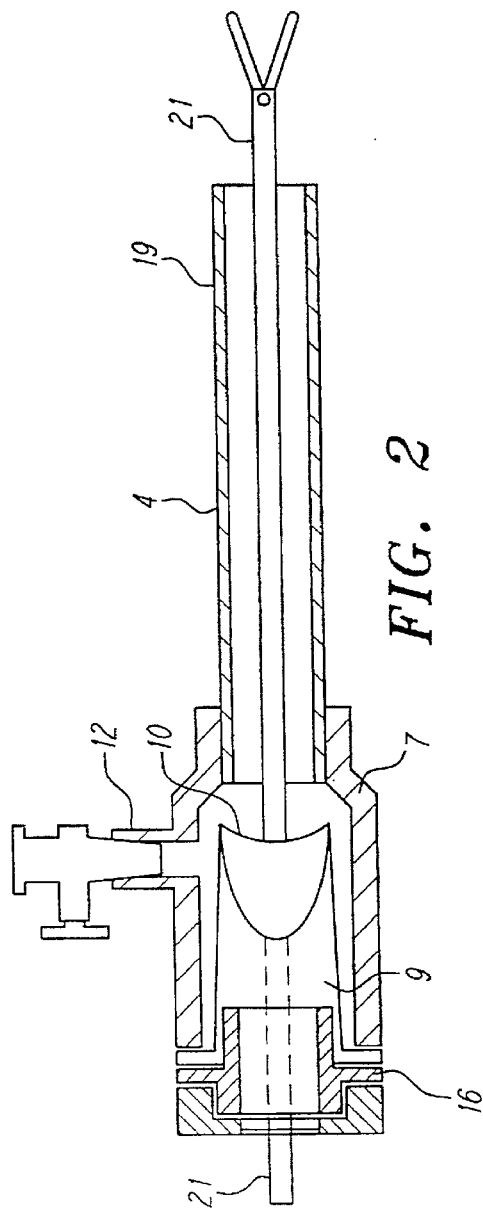

CANNULA ASSEMBLY WITH SQUEEZE OPERATED VALVE

FIELD OF THE INVENTION

This invention relates to methods and devices for endoscopic surgery and improved valves for skin seals and endoscopic access ports.

BACKGROUND OF THE INVENTION

Surgical endoscopy is a surgical technique of using small-diameter long-handled tools such as graspers, forceps, scissors, retractors, dissectors and clamps specially designed to be inserted through small incisions in the skin (or other openings in the body) to perform operations within the body. The surgeon performing the surgery often cannot see the operation directly, and must watch the procedure on a video monitor fed by an endoscopic camera or endoscope. Endoscopic surgery replaces open surgery, which requires large incisions, essentially opening the body cavity completely, in order to perform surgery deep within the body. Endoscopic techniques have been used for gall stone removal, gall bladder removal, hernia repair, tumor removal, lymph node removal and appendectomy and many other operations. Endoscopic surgery is also called laparoscopic surgery, video assisted surgery, minimally invasive surgery, and band-aid surgery, but throughout this specification the term endoscopic surgery or laparoscopic surgery will be used.

In endoscopic surgery, a working space was created in the abdomen using the process called pneumoperitoneum or insufflation. Insufflation is the process of injecting gas into the body to blow it up like a balloon, creating a chamber filled with gas. When performed on the abdomen, the peritoneum is inflated and the procedure is known as pneumoperitoneum. The procedure can be used for inflating a space between the peritoneum and the skin to permit laparoscopic hernia repair, as illustrated in Keiturakis and Mollenauer, Apparatus and Method for Developing and Anatomic space for laparoscopic hernia repair, U.S. Pat. No. 5,496,345. Insufflation can be used also to inflate a tunnel shaped working space over a blood vessel, to facilitate blood vessel harvesting, as described in Fogarty, et al., Methods and Devices for Blood Vessel Harvesting, U.S. application Ser. No. 08/475,137, incorporated herein by reference. While the chamber is filled with gas, the surgeon inserts long slender laparoscopic tools through trocars and cannulas which pierce the skin and provide access ports into the insufflated chamber.

For abdominal surgery such as a cholecystectomy (gall bladder removal), the insufflation is accomplished by the following procedure. An incision is made at the lower edge of the belly button or umbilicus. The surgeon uses his fingers or a blunt dissection tool such as a blunt nosed obturator to uncover the fascia or abdominal muscles, then a large needle, referred to as a Verres needle is inserted into the abdomen or peritoneal cavity. The Verres needle punctures the fascia and peritoneum which cover the abdomen. A pressurized gas such as $CO_2$, nitrous oxide or other suitable gas or liquid is injected into the abdomen through the needle, in effect inflating the abdomen like a balloon. After the abdomen is inflated, the Verres needle is removed. After the needle is removed, trocars and cannulas are inserted into the space created by the insufflation. Endoscopic instruments including an endoscope or laparoscope, scissors, graspers, etc., are inserted into the abdomen through the cannulas and manipulated to dissect tissue surrounding the gall bladder, remove the gall bladder, and stitch the internal wounds.

To harvest the saphenous vein using laparoscopic procedures, the surgeon may insufflate a tunnel shaped work space over a blood vessel. The tunnel is first created using obturators or tunneling devices or balloons inserted through small incisions along or over the saphenous vein. After the tunnel is created, the surgeon may insert skin seals and cannulas, and insufflation gas is injected through one of the trocars. While the tunnel is insufflated, the cannulas permit the surgeon to insert laparoscopic instruments into the tunnel to perform surgery on the saphenous vein.

The cannula used in the procedures described above is a length of rigid tube. The cannulas are typically about 6 inches or 15 centimeters long, and come in diameters matching various laparoscopic devices, generally from 2 to 15 mm. The trocars and cannula are designed to allow laparoscopic instruments to pass through them and prevent gas from escaping the abdomen or other insufflated work space. The cannula may have a flapper valve or a trumpet valve inside which opens to allow an endoscope or laparoscope or other instrument to pass through, and the valve closes against an access tube when the laparoscope is removed. A typical cannula flapper valve is illustrated in Stephens, et al., U.S. Pat. No. 5,197,955 entitled Universal Seal for Trocar Assembly. Some trocar/cannula devices also contain a duckbill valve to assist in sealing the trocar. A duckbill valve used to seal a cannula is illustrated in Kayan and Mollenauer, Cannula with Improved Valve and Skin Seal, U.S. Pat. No. 5,324,270. Another form of duckbill valve is illustrated in Durman, Self Sealing Flexible Elastomeric Valve and Trocar Assembly for Incorporating Same, U.S. Pat. No. 5,330,437, which refers to the duckbill valve as a self sealing valve. These references show the valves within rigid plastic housings.

The surgeon usually needs to place several trocars and cannulas into the insufflated workspace, and inserts as many as needed to accomplish the intended operation. If two or more cannulas are in place, the surgeon can view the procedure through any port, and can insert laparoscopic scissors, cutters and graspers and other tools through the cannulas in order to perform the surgery. Endoscopic and laparoscopic instruments of various designs are available, and they generally are about 5 to 12 mm in diameter (to match the inside bore of the cannulas) and about 10 to 40 cm in length. The tip of these endoscopic instruments may can a wide variety of working elements such as graspers, clip appliers, knot tying devices, scissors and snippers, electrocautery devices and more. Many of these instruments have structures at their tips which are of non-uniform diameter and odd or irregular shape, and these structures may catch or snag the flapper valve or duckbill valve upon withdrawal. When an instrument gets caught up on the valve, the surgeon must operate the valve handle to fully open the valve and allow the instrument to pass backwards out of the cannula. In the case of duckbill valves, no valve handle or operating mechanism is provided, so that excessive force may be required to pull the instrument backwards through the valve. The valve manipulation and excessive force are inconvenient, and may even require assistance from another surgeon. The valve manipulation and excessive force may also result in inadvertent removal of a cannula, further causing loss of insufflation pressure and possible injury to the patient as the insufflated work space collapses upon the tools and cannulas in place and as the cannula is re-installed into the body.

SUMMARY OF THE INVENTION

The endoscopic access cannula with a squeezable valve disclosed herein consists of a cannula which is sized to match standard endoscopic and laparoscopic instruments. The handle portion of the cannula is fitted with a duckbill valve or other squeezable valve, and the cannula housing itself (or portion of the cannula housing) is made of rubber or other resilient elastic material. Squeezing the cannula housing also squeezes the duckbill valve and causes it to open, thereby allowing an endoscopic instrument to be pulled backward through the duckbill valve without getting snagged on the duckbill valve.

BRIEF DESCRIPTION OF THE DRAWINGS

FIG. 1 shows the squeezable duckbill valve housing on a typical cannula and cannula handle assembly FIG. 2 shows the squeezable duckbill valve in its open position with an endoscopic instrument inserted through the valve.

DETAILED DESCRIPTION OF THE DRAWINGS

Figure 3:
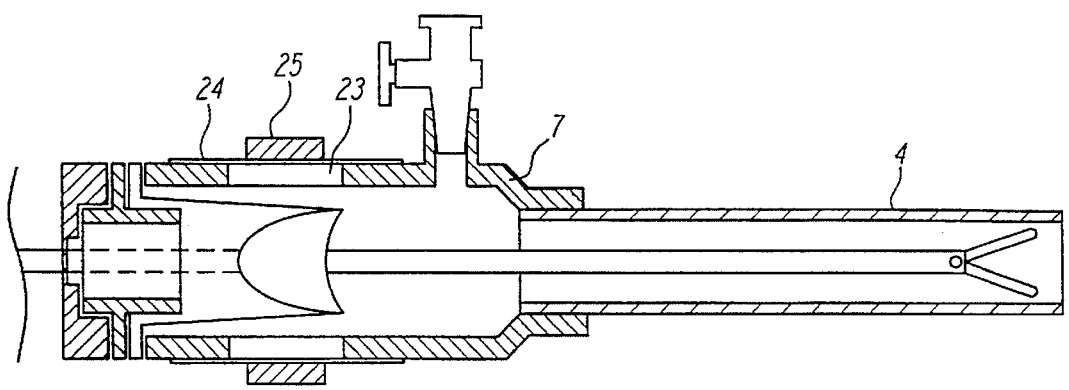
FIGS. 3 and 3a shows show an alternative embodiment of the squeeze operated cannula valve

FIG. 1 shows a cannula assembly 3 including a cannula 4 with a cannula handle 5 fitted with a duckbill valve 6 inside the valve housing 7. The duckbill valve has two flaps, leaflets, or bills 8 which are closed when in the relaxed state, but will resiliently yield and open when an instrument is pushed through the valve. The operating mechanism for the duckbill valve is the side wall portion 9 which can be compressed to separate the duckbill valve leaflets. The duckbill valve leaflets have a distal face 10 and a proximal face 11. The leaflets may variously be referred to as flaps, duckbills, sealing walls, truncate side walls, etc. The handle has a valve housing 7 around the duckbill valve. The housing may be cylindrical or box shaped or any other convenient shape. The housing has an insufflation port 12 which enters the housing downstream of the valve and communicates with the cannula. A stopcock 13 is provided in the insufflation line extending from the insufflation port. A downstream section 14 or pressure side of the cannula housing is located on the distal side of the valve. This section is pressurized during insufflation. The cannula handle may also include a membrane seal or ring seal 15 which fits tightly around instruments passed through the cannula and provides a further seal. A pipe joint 16 provides mounting structures for the duckbill valve and the ring seal. An end cap 17 may be provided, and the end cap and other parts may be secured by compression fit, adhesives, heat sealing or integral construction. The trocar handle 18 fits onto the end cap and may be fitted with a trocar or blunt obturator which extends through the cannula assembly.

In operation, the cannula assembly 3 is pushed through a small incision in the skin into a working space in the body. The working space may be insufflated before or after the cannula is inserted. The distal end 19 of the cannula is pushed into the body while the cannula assembly 3 is held by the handle 5 on the proximal end 20. Once in place, endoscopic instruments such as cutters 21 may be inserted through the cannula, into the proximal end, as shown in FIG. 2, passing through ring seal at the proximal end of the assembly, passing through the duckbill valve and extending out the distal end 19. The endoscopic instrument meets the proximal or back faces of the duckbill leaflets and pushes the valve open, and the duckbill leaflets or sealing walls resiliently conform around the instrument to create an airtight seal around the instrument. The instrument is further pushed forward (or distally) through the cannula until it enters the endoscopic workspace. While the cannula assembly is in place, the endoscopic work space may be insufflated through insufflation port 12 on the housing 7. The valve or stopcock 13 is open during insufflation and closed to seal the housing when the insufflation port is not in use. Insufflation fluid injected under pressure into the housing will flow into the body through the cannula, and will exert force upon the distal or front faces 10 of the duckbill valve leaflets 8 and hold them closed. Insufflation pressure provided through another cannula will also exert force on the duckbill valve leaflets to hold them closed and create a seal for the insufflated work space.

The surgeon may remove the endoscopic instrument by pulling it backward, or proximally, out of the work space and through the cannula assembly. To guard against pulling the entire assembly out of the body and completely deflating the insufflated work space, the surgeon will grasp the valve housing 7 while pulling gently on the endoscopic instrument. The duckbill valve will usually allow the instrument to pass through with minimum resistance, but sometimes the edge or lip 22 will snag some structure of the endoscopic instrument. To overcome such snags, the entire housing 7 shown in FIGS. 1 and 2 is made of silicone rubber or other pliant and elastic material, and the duckbill valve is operable by squeezing the entire housing until the duckbill valve itself is compressed to open the leaflets. With the leaflets separated, the endoscopic instruments pass easily through the valve and any snagging is avoided or cleared. Thus, removal of an endoscopic instrument which may be obstructed by the valve leaflets is permitted, and accomplished merely by squeezing the housing. Because the surgeon is already holding the housing in his hand, no extra manipulations are necessary, and the removal of instruments is simplified over the operation of flapper valves and made safer over removal permitted by passive duckbill valves.

The various parts of the squeezable valve may be made from a wide variety of materials. The elastic membrane and the squeezable housing may be made from silicone rubber, polyethylene, latex rubber, PVC, urethane polymers, vinyl polymers and any other suitable elastomeric material which is sufficiently flexible to allow squeeze operation with a comfortable degree of effort. The duckbill valves and flapper valves may likewise be made of a wide variety of elastomeric and plastic materials.

Figure 3A:
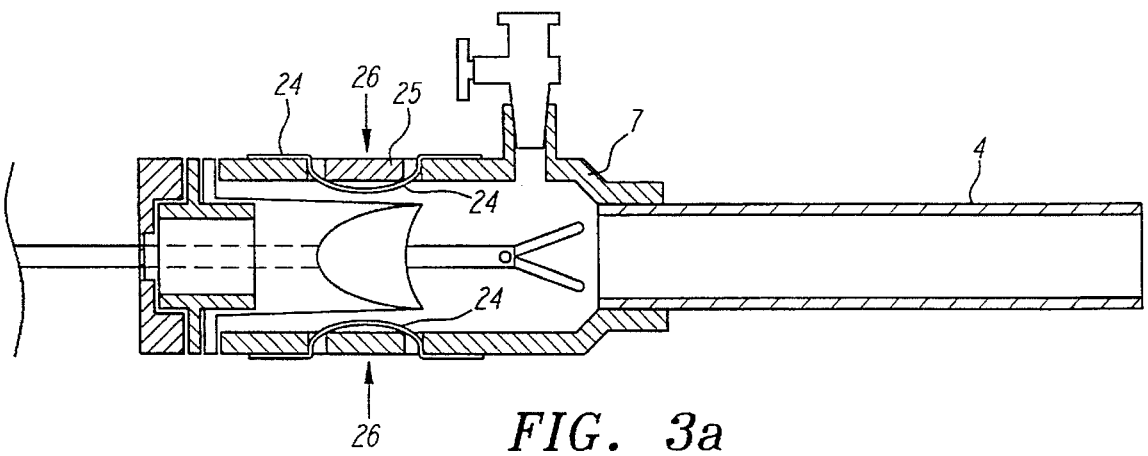
Figure 4:
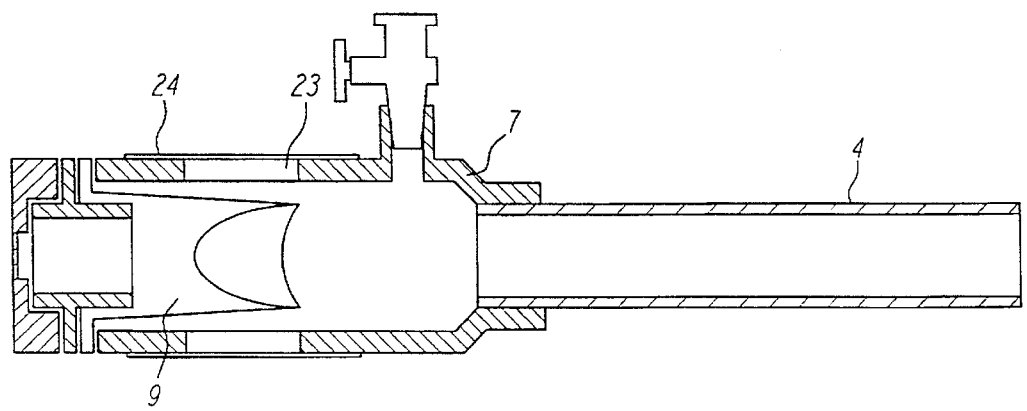
FIG. 4 shows an alternative embodiment of the squeeze operated cannula valve.
Figure 5:
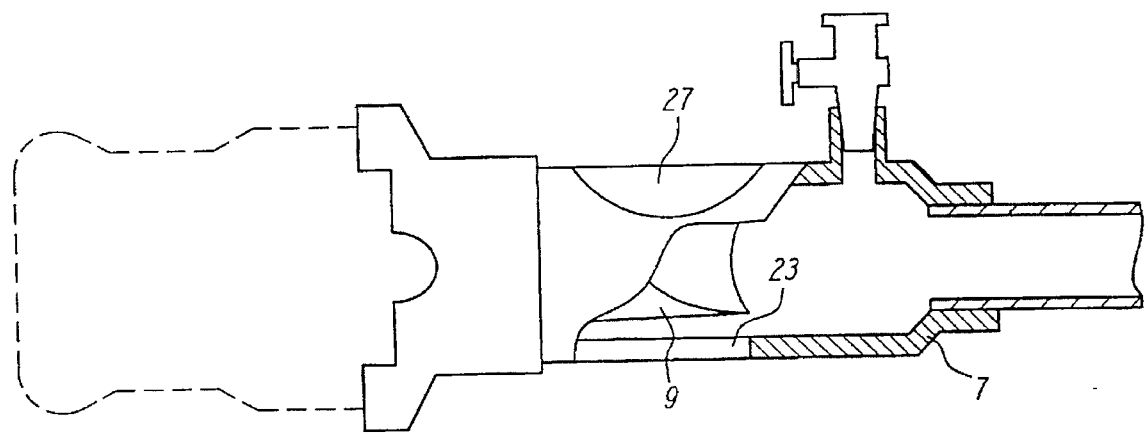
FIG. 5 shows an alternative embodiment of the squeeze operated duckbill valve
Figure 6:
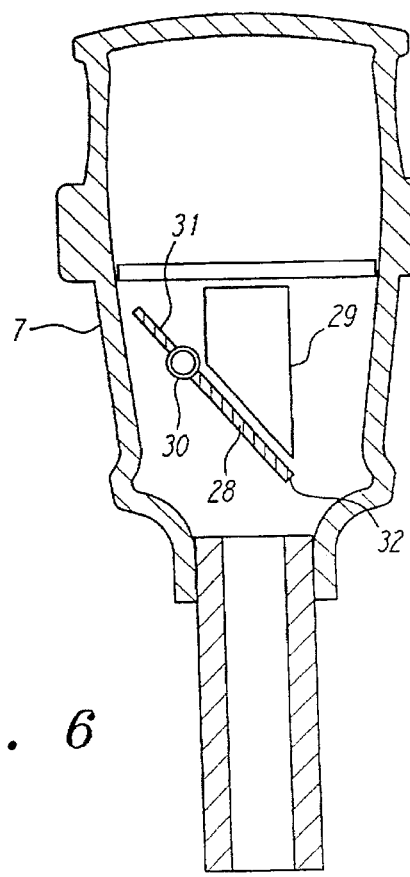
FIG. 6 shows a squeeze operated flapper valve inside a typical cannula assembly

It will be apparent that the squeezable valve may be made in many embodiments, all of which are intended to be covered by the claims presented below. A few illustrations are presented to show the variety of embodiments which may be envisioned for application of a squeeze valve. FIG. 3 shows the cannula assembly with the duckbill valve inside which may be compressed to open using the two squeeze holes 23 one on either side of the housing, aligned with the lip of the duckbill valve. The squeeze holes are covered with an elastic sleeve membrane or wide rubber band 24, and the rubber band is further fitted with squeezing blocks 25. The housing in this embodiment is rigid. When the surgeon squeezes the blocks in the direction indicated by arrows 26, the blocks enter the housing and squeeze the duckbill valve and forces the leaflets to separate, as shown in FIG. 3a. FIG. 4 shows the squeezable valve of FIG. 3, altered by removal of the squeeze blocks. In this embodiment, the surgeons own fingers press the elastic sleeve 24 into the housing and into contact with the duckbill valve. In FIG. 5, the elastic sleeve is replaced with elastic membranes 27 covering the squeeze ports, providing airtight seal of the squeeze ports while being sufficiently elastic to permit operation of the duckbill valve through the elastic membranes. In FIG. 6, the housing is similar to that shown in FIGS. 1 and 2, but the traditional flapper valve 28 is used. The flapper valve is spring loaded so that it rests against the access tube 29, and is self sealing because the spring 30 urges the flap into a closed position against the access tube. The flapper valve is modified by provision of an operating lever 31 placed inside the housing and under the squeezable housing 7 covered by the elastic sleeve membrane. Pressure on the housing over the operating lever will result in operation of the flapper valve lever to hold the flap open so the instruments may be pulled proximally out of the cannula without catching on the distal edge 32 of the flapper valve.

Thus the introduction and withdrawal of endoscopic instruments through a sealed endoscopic access cannula is facilitated by provision of the squeezable valve which may be operated with little more effort than is required to hold the cannula for withdrawal of the instruments. Because the valve may be operated single-handedly, the process of removing an endoscopic instrument from an insufflated work space is made simpler, easier and safer. It will be readily apparent that many embodiments of the squeezable valve are possible, and that the squeezable valve may be constructed in a variety of embodiments without departing from the spirit of the invention or the scope of the claims presented below.

I claim:

1. A valve housing for a cannula assembly having a cannula with a distal end and a proximal end, the valve housing being disposed on the proximal end of the cannula, said valve housing containing a valve with a distal side and a proximal side, said valve providing a substantially airtight seal to maintain high pressure on the distal side of the valve, said valve capable of permitting passage of endoscopic instruments through the valve and into the cannula, said valve housing comprising compressible valve operating means for converting compressive force upon a portion of the valve housing to operating action on the valve.

2. A method for inserting and withdrawing endoscopic instruments into the body through a cannula, said method comprising:
providing an cannula with a valve adapted to receive the endoscopic instruments, said valve being disposed within a valve housing, said valve housing having compressible means for opening and closing the valve;
compressing the compressible means to operate the valve while withdrawing an endoscopic instrument from the cannula, thereby avoiding obstruction of the endoscopic instrument by the valve.

3. A method for inserting and withdrawing endoscopic instruments into the body through a cannula, said method comprising:
providing an cannula with a valve adapted to receive the endoscopic instruments, said valve being disposed within a valve housing, said valve housing having a flexible portion which may be squeezed into contact with the valve to operate the valve;
compressing the flexible portion to operate the valve while withdrawing an endoscopic instrument from the cannula, thereby avoiding obstruction of the endoscopic instrument by the valve.

4. A cannula assembly for receiving a surgical instrument comprising:
a cannula;
a valve housing on the proximal end of said cannula;
a valve disposed within said valve housing;
said valve housing having a movable wall portion; and
said movable wall portion adapted to be moved into contact with said valve to open said valve to permit the surgical instrument to be withdrawn from the cannula.

5. The cannula assembly of claim 4 wherein said valve is a self sealing valve.

6. The cannula assembly of claim 4 wherein said valve is a duckbill valve.

7. The cannula assembly of claim 4 wherein said valve is a flapper valve.

8. A cannula assembly for receiving a surgical instrument comprising:
a cannula;
a valve housing on the proximal end of said cannula;
a valve disposed within said valve housing;
said valve housing having a flexible wall portion; and said flexible wall portion adapted to be moved into contact with said valve to open said valve to permit the surgical instrument to be withdrawn from the cannula.

9. The cannula assembly of claim 8 wherein said valve is a self sealing valve.

10. The cannula assembly of claim 8 wherein said valve is a duckbill valve.

11. The cannula assembly of claim 8 wherein said valve is a flapper valve.

12. A cannula assembly comprising:
a cannula;
a valve housing on the proximal end of said cannula;
a valve disposed within said valve housing; and
said valve housing having a squeeze port, said squeeze port covered by an elastic membrane, said elastic membrane being capable of being moved into said squeeze port and into contact with said valve to actuate said valve.

13. A cannula assembly comprising:
a cannula;
a valve housing on the proximal end of said cannula;
a valve disposed within said valve housing;
said valve housing having a squeeze port, said squeeze port covered by an elastic membrane, said squeeze port being large enough to permit said elastic membrane to be moved into contact with said valve to actuate said valve; and
a squeeze block operably connected to said elastic membrane so that squeezing force on said squeeze block moves said elastic membrane into said squeeze port and into contact with said valve actuating said valve.

14. A cannula assembly comprising:
a cannula;
a valve housing on the proximal end of said cannula;
a valve disposed within said valve housing; and
said valve housing having a squeeze port, said squeeze port covered by an elastic membrane, said elastic membrane comprising an elastic band surrounding said valve housing, said elastic membrane being capable of being moved into said squeeze port and into contact with said valve to actuate said valve.

* * * * *

UNITED STATES PATENT AND TRADEMARK OFFICE
CERTIFICATE OF CORRECTION

PATENT NO. : 5,643,301
DATED : July 1, 1997
INVENTOR(S) : Kenneth H. Mollenauer

It is certified that error appears in the above-identified patent and that said Letters Patent is hereby corrected as shown below:

In claim 4, column 6, line 6, delete "movable" and insert therefor --squeezable--.

In claim 4, column 6, line 7, delete "movable" and insert therefor --squeezable--.

Signed and Sealed this

Twenty-fourth Day of November, 1998

Attest:

BRUCE LEHMAN

*Attesting Officer*    *Commissioner of Patents and Trademarks*